US011331503B2

United States Patent
Kast et al.

(10) Patent No.: US 11,331,503 B2
(45) Date of Patent: *May 17, 2022

(54) MODULAR SHIELD EXTENDER

(71) Applicant: MEDTRONIC, INC., Minneapolis, MN (US)

(72) Inventors: John E. Kast, Hugo, MN (US); Linda M. Johnson-Morke, Isanti, MN (US); Chris J. Paidosh, St. Anthony, MN (US); Randy S. Roles, Elk River, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 58 days.

This patent is subject to a terminal disclaimer.

(21) Appl. No.: 16/882,644

(22) Filed: May 25, 2020

(65) Prior Publication Data

US 2020/0282221 A1 Sep. 10, 2020

Related U.S. Application Data

(63) Continuation of application No. 15/942,272, filed on Mar. 30, 2018, now Pat. No. 10,661,088, which is a continuation of application No. 15/478,187, filed on Apr. 3, 2017, now Pat. No. 9,956,420, which is a continuation of application No. 14/926,890, filed on Oct. 29, 2015, now Pat. No. 9,610,453.

(60) Provisional application No. 62/073,648, filed on Oct. 31, 2014.

(51) Int. Cl.
*A61N 1/375* (2006.01)

(52) U.S. Cl.
CPC ........... *A61N 1/3754* (2013.01); *A61N 1/375* (2013.01); *A61N 1/3758* (2013.01)

(58) Field of Classification Search
None
See application file for complete search history.

(56) References Cited

U.S. PATENT DOCUMENTS 7,751,893 B2 * 7/2010 Biggs, Jr. ............. A61N 1/3752
607/36
2009/0192578 A1 * 7/2009 Biggs ................... A61N 1/3752
607/116

OTHER PUBLICATIONS

EP Application No. 15 790 802.1 Office Action, dated Jan. 13, 2021.

* cited by examiner

*Primary Examiner* — Brian T Gedeon
(74) *Attorney, Agent, or Firm* — Withers & Keys, LLC

(57) ABSTRACT

An implantable medical device (IMD) has a housing enclosing an electronic circuit. The housing includes a shield member defining a first portion of an interior cavity of the implantable medical device and a skirted feedthrough assembly. The feedthrough assembly includes a shield extender having a top face and a sidewall that extends from the top face so that the top face and the sidewall are a single continuous component. At least one feedthrough aperture extends through the top face.

20 Claims, 7 Drawing Sheets

MODULAR SHIELD EXTENDER

RELATED APPLICATIONS

This application is a continuation of U.S. Pat. No. 10,661,088, filed on Mar. 30, 2018, which is a continuation of U.S. Pat. No. 9,956,420, filed on Apr. 3, 2017, which is a continuation of U.S. Pat. No. 9,610,453, filed on Oct. 29, 2015, which claims priority to U.S. Provisional Application No. 62/073,648, filed on Oct. 31, 2014.

FIELD

The disclosure relates generally to implantable medical devices and in particular to a housing of an implantable medical device having a feedthrough assembly with a shield extender.

BACKGROUND

Implantable medical devices (IMDs) for sensing physiological signals and/or delivering automatic therapies are available for a number of medical applications for monitoring and/or treating medical conditions. In order to promote patient comfort, biocompatibility, and enable minimally invasive implantation procedures, in certain situations it may be desirable to reduce the overall size of an IMD and provide smooth, rounded exterior contours of the IMD housing. Reduced-size housings, with smooth contoured shapes, however, can increase manufacturing complexity and/or cost of the IMD.

DETAILED DESCRIPTION

Applicants have an appreciation that implantable medical device (IMD) technology is continually advancing as new applications are developed for patient monitoring and automated therapy delivery in patients. Such advances may be further enhanced by using devices of reduced size and weight, which may make implantation of such devices less invasive and chronic use more comfortable for the patient. Accordingly, Applicants recognize in some applications there is a need for improved, minimally-invasive implantable medical device systems, and associated methods of use for providing patient monitoring and/or automatic therapy delivery. Certain exemplary embodiments disclosed herein may obtain some or all of the aforementioned advantages and enhancements.

In the following description, references are made to illustrative embodiments. Various embodiments of housing for an IMD included in an implantable neurostimulation (INS) system for delivering an electrical stimulation therapy to a targeted neural site are described. However, it is recognized that the various embodiments of the housings described herein may be implemented in numerous types of IMDs, including, for example, implantable sensors, implantable communication devices, and other types of implantable therapy delivery systems. The various embodiments of IMD housings described herein and associated methods of manufacture will reduce size and/or cost of the device and promote and facilitate minimally invasive implantation procedures in which the incision size and time required to implant and anchor the device can be minimized.

Figure 1:
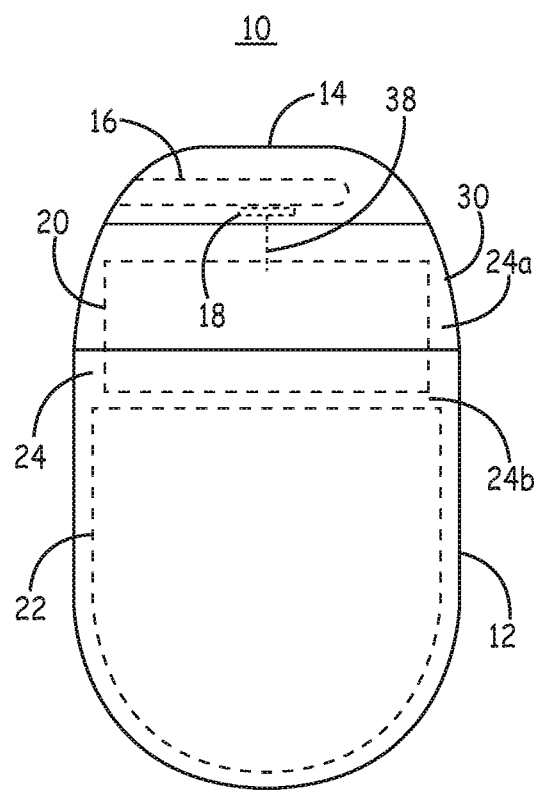
FIG. 1 is a conceptual diagram of an IMD according to one exemplary embodiment.

FIG. 1 is a conceptual diagram of an IMD 10 according to one exemplary embodiment. IMD 10 includes a shield member 12 for enclosing internal IMD circuitry. Shield member 12 is coupled to a feedthrough assembly 30. A connector block 14 is coupled to the feedthrough assembly 30. Connector block 14 includes one or more connector bores 16 for receiving a connector pin of a medical electrical lead (not shown). For example, bore 16 may be sized to receive an industry standard medical lead connector pin such as an IS-4 or other industry standard or custom lead connector pin. One or more electrical contacts 18 extend along bore 16 for making electrical connection to a lead connector pin inserted within bore 16. In some examples, contacts 18 are molded within connector block 14 and coupled to a conductive trace that extends to a feedthrough pin 38 extending through feedthrough assembly 30. Feedthrough assembly 30 includes at least one electrical feedthrough pin 38, i.e., feedthrough pin 38 is an electrically conductive pin, extending from contact 18 to a hybrid circuit 20 enclosed within feedthrough assembly 30 and/or shield member 12. Feedthrough pin 38 carries electrical signals across shield member 12. A battery 22 is coupled to hybrid circuit 20 for powering IMD functions and is shown enclosed within shield member 12.

The interior cavity 24 of IMD 10 includes a first portion 24a defined by feedthrough assembly 30 and a second portion 24b defined by shield member 12. The first portion 24a is in open communication with the second portion 24b to define a single interior cavity 24 of the IMD 10 for housing the hybrid circuit 20 and battery 22 in some examples. In other examples interior cavity 24 for housing hybrid circuit 20 is separated from a battery cavity for housing battery 22 with necessary electrical connections extending between the separate cavities.

Figure 2:
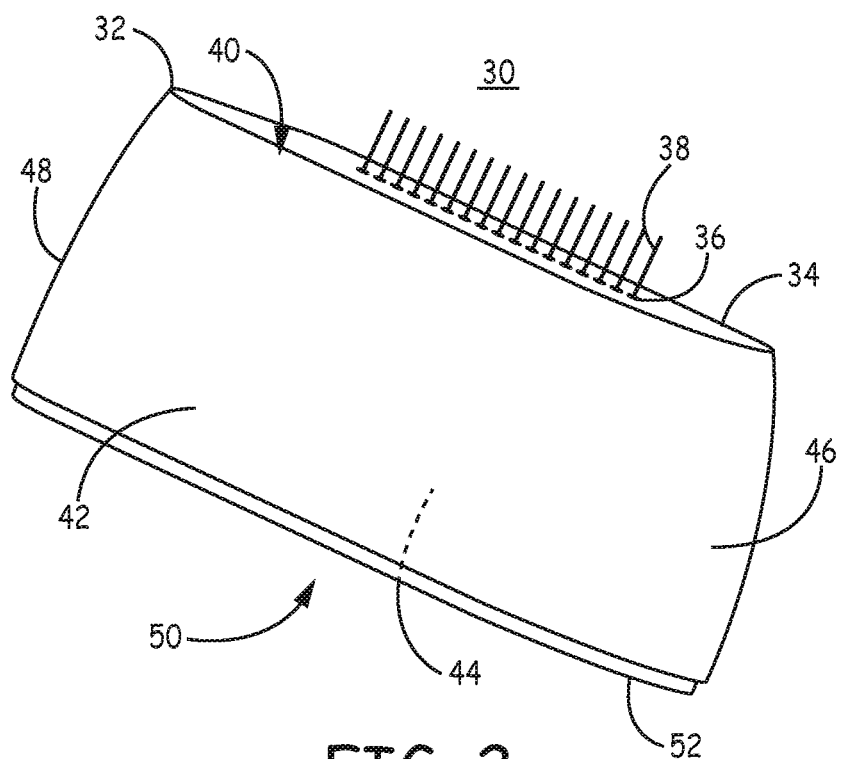
FIG. 2 is a perspective view of an exemplary feedthrough assembly included in the IMD of FIG. 1.

FIG. 2 is a perspective view of feedthrough assembly 30. Feedthrough assembly 30 includes a shield extender 32 having a top face 34 and a sidewall 40 having major opposing sides 42 and 44 (not seen in the view of FIG. 2) and contoured minor sides 46 and 48 having a smooth rounded shape without sharp edges or corners. Major sides 42 and 44 are separated by top face 34. Feedthrough assembly 30 is a "skirted" feedthrough assembly in that sidewall 40 circumscribes top face 34, extends downward from top face 34 to define interior cavity first portion 24a (shown in FIG. 1) of IMD 10.

Shield extender 32 thereby extends the interior cavity of the IMD defined by shield member 12 as well as provides feedthrough apertures 36 for passing electrically conductive feedthroughs 38 from connector block 14 (FIG. 1) to the interior cavity 24 of IMD 10. Top face 34 includes at least one feedthrough aperture 36. An electrically conductive feedthrough pin 38 extends through each aperture 36 and is electrically insulated from shield extender 32.

Shield extender 32 includes an open bottom side 50, opposite top face 34, defined by a bottom edge 52 of sidewall 40. Bottom edge 52 extends continuously along major sides 42, 44 and minor sides 46, 48 of sidewall 40 and forms a mating surface for joining feedthrough assembly 30 to shield member 12. Accordingly, bottom edge 52 may include an underlapping or overlapping flange, sloped edge, or other mating geometry that interfaces with a corresponding geometry of shield member 12. Bottom edge 52 may be welded or sealed to shield member 12, e.g. using laser welding, brazing, fusion bonding, or other sealing methods appropriate for use with the materials used to form shield extender 32 and shield member 12.

Sidewall 40 defines the interior cavity 24a (shown in FIG. 2) within feedthrough assembly 30 that extends the interior volume of IMD 10 defined by shield member 12 for housing hybrid circuit 20 and battery 22. The interior cavity 24 of IMD 10 therefore includes a first portion 24a defined by shield member 12 and a second portion 24b defined by shield extender 32. The first portion 24a is in open communication with the second portion 24b to define a single interior cavity 24 of the IMD 10 for housing the hybrid circuit 20 and battery 22 in some examples.

Shield extender 32 having top face 34 and sidewall 40 is a single component having feedthrough apertures extending through top face 34 such that no separate ferrule or feedthrough plate is required in some examples. Feedthrough assembly 30 differs from feedthrough assemblies that include a ferrule that is welded into an opening in an IMD housing in that shield extender 32 is a single continuous piece that defines the feedthrough apertures 36 as well as both interior and exterior surfaces of the IMD housing. In these instances, shield extender 32 is a single, machined or metal injection molded component. Shield extender 32 may be fabricated from, without limitation, titanium, stainless steel, or alloys thereof. For example, shield extender 32 may be machined from Grade 5 titanium. A higher alloy titanium provides higher resistivity and reduces heat generated and IMD hybrid circuit interference caused by electromagnetic (EM) noise, such as during Magnetic Resonance Imaging (MRI). Other examples of titanium alloys that may be appropriate for fabrication of shield extender 32 include, with no limitation intended, Grade 38 (Ti 4 AL 2.5 V), Grade 9 (Ti 3 Al 2 V) and Ti 8 AL 1 Mo 1V alloy. In other examples, shield extender 32 may be a ceramic, glass or polymeric material. Shield member 12 may be fabricated from the same or a different material than shield extender 32.

Figure 3:
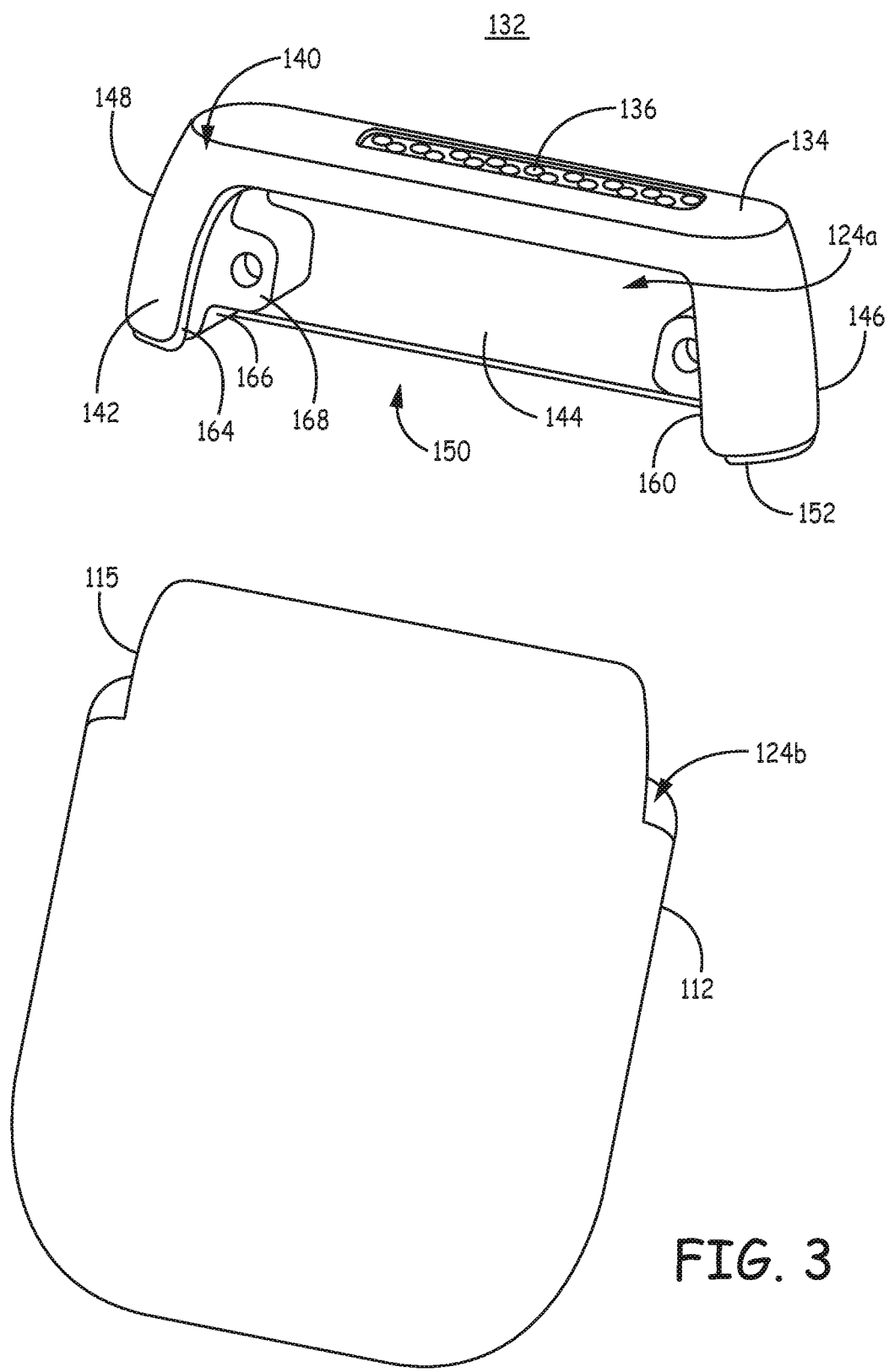
FIG. 3 is a perspective view of an alternative exemplary embodiment of a shield extender for use in a feedthrough assembly of an IMD and an associated shield member.

FIG. 3 is a perspective view of an alternative example of a shield extender 132 for use in a feedthrough assembly of an IMD and an associated shield member 112. Shield extender 132 includes a top face 134 and a sidewall 140 extending from the top face 134 to a bottom edge 152. Bottom edge 152 defines an open bottom side 150. The sidewall 140 includes major opposing sides 142, 144 and contoured minor opposing sides 146, 148. Sidewall 140 and top face 134 define a first portion 124a of an interior cavity of the IMD when shield extender 132 is assembled with shield member 112.

Sidewall 140 includes a channel 160 extending into major side 142 defining an opening or window providing access to the interior portion 124a of the IMD interior cavity prior to sealing shield extender 132 and shield member 112. A channel 160 or other opening along one or more of major sides 142, 144 and/or minor sides 146, 148 provides access for assembling a hybrid circuit, battery or other internal IMD component within the interior portion 124a of the IMD internal cavity. For example, channel 160 may provide access for making electrical connections between a hybrid circuit and feedthrough pins extending through feedthrough apertures 136 of the top face 134 of shield extender 132. The channel 160 may include an underlapping edge 164, which may be continuous with an underlapping edge of bottom edge 152 for interfacing with shield member 112.

A single channel 160 in sidewall 140 is illustrated in FIG. 3. Channel 160 is shown to extend along a major side 142 and extend for more than a majority of the width and height of major side 142. It is contemplated, however, that one or more channels may be defined by sidewall 140 which may extend along any portion of one or more of major sides 142, 144 and/or minor sides 146, 148 and may extend for any portion of the height or width of the sidewall, e.g. less than or more than a majority of the height and/or width of the side. In one example, opposing major side 144 includes a channel identical to channel 160 of major side 142 such that the major sides are symmetrical.

An inner surface 166 of sidewall 140 may include an interior coupling member 168 for attaching internal IMD components, such as a hybrid circuit board. Coupling member 168 is shown as a receptacle for receiving a fastening member in the example of FIG. 3. Coupling member 168 may be a threaded screw hole in some examples. In other examples, coupling member 168 may be a post, rail, ridge, groove, ledge, or other member for attaching, supporting or guiding the location of an internal IMD component, such as the hybrid circuit board, or the mating shield member 112. Coupling member 168 may protrude into interior cavity portion 124a, interior cavity portion 124b defined by shield member 112, or both. A pair of opposing receptacles for receiving a fastening member is shown in FIG. 3. Shield extender 132 may include one or more coupling member extending from inner surface 166 of any of the major sides 142, 144, minor sides 146, 148, and/or top face 134, which may include one or more fastening member receptacles, posts, rails, ridges, grooves, ledges, or other guiding, supporting or attachment member. Shield extender 132 including feedthrough apertures 136, channel 160 and interior coupling member(s) 168, may be machined as a single component from a block of raw material, such as Grade 5 Titanium or other examples listed previously herein.

Shield member 112 includes a flange 115 having a male geometry to match the female geometry of channel 160. Shield member 112 defines a second portion 124b of an interior cavity that communicates with the first portion 124a defined by shield extender 132. The underlapping edge 164 of shield member sidewall channel 160 acts as supporting ledge against which shield member flange 115 rests when assembling shield extender 132 and shield member 112 together. Underlapping edge 164 and a corresponding overlapping edge of flange 5 define a seam along which extender 132 and member 112 are sealed together. Underlapping edge 164 may facilitate welding of flange 115 to shield extender 132 and serve to reduce welding energy reaching internal circuitry.

Figure 4:
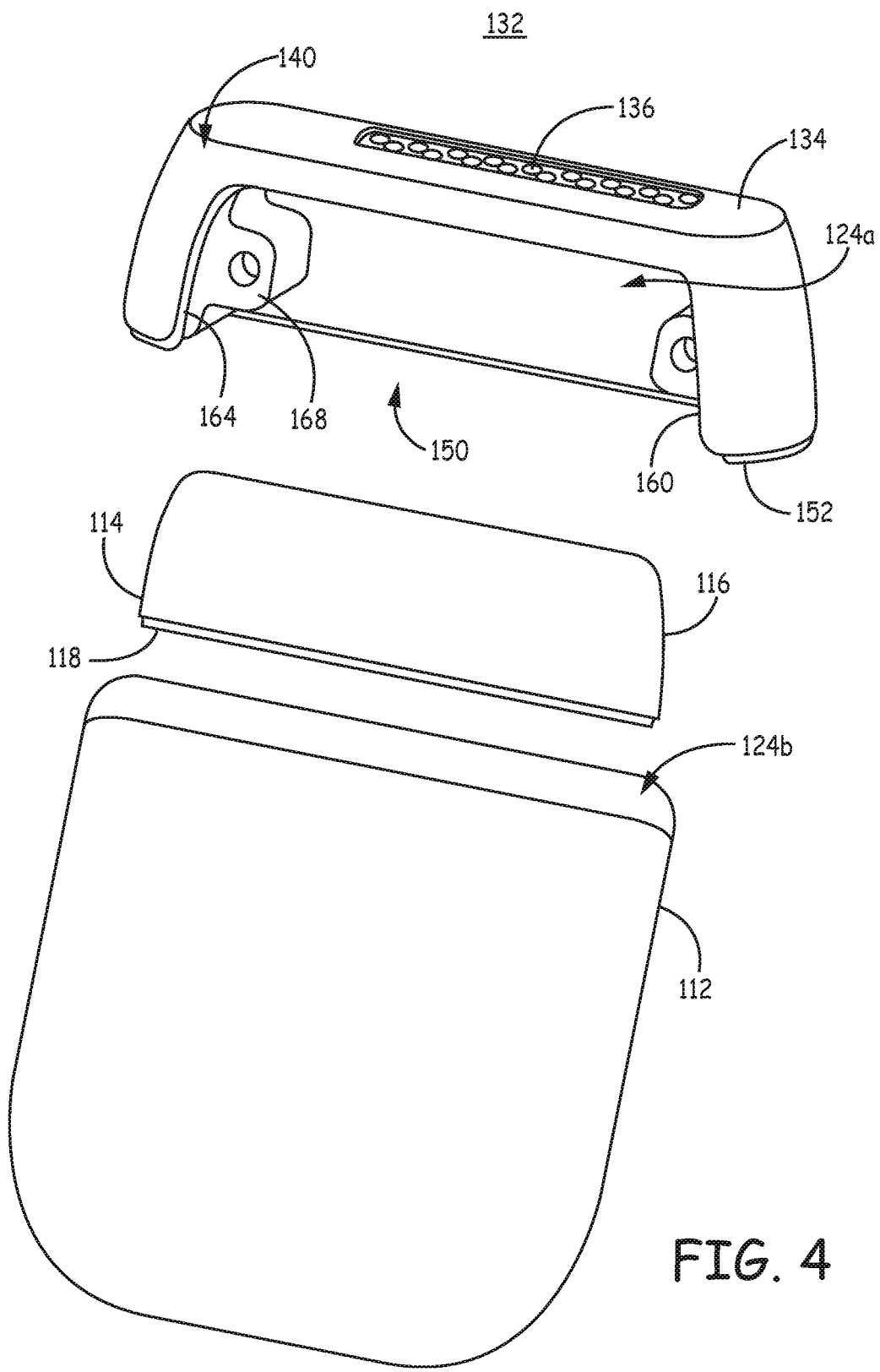
FIG. 4 is an alternative exemplary embodiment of the shield member and shield extender shown in FIG. 3.

FIG. 4 is an alternative embodiment of the shield member and shield extender shown in FIG. 3. In FIG. 3, shield extender 132 and shield member 112 form a two-part assembly that defines the interior cavity of the IMD for housing a battery and circuitry. In FIG. 4, a channel cover 114 is provided as a third part for assembling over sidewall channel 160 of shield extender 132. While the examples of FIGS. 3 and 4 are referred to, respectively, as two-part and three-part assemblies that define the interior IMD cavity, it is recognized that, in some examples, shield members 12 and 112 may include two shield member halves that are welded or otherwise joined together to form the single shield member 12 or 112.

In the example of FIG. 4, shield member 12 and shield extender 132 can be assembled together with channel 160 remaining open to provide access to interior cavity portion 124a for making various mechanical and/or electrical connections between a battery, hybrid circuit board, feedthrough pins, coupling member 168, etc. and to enable testing of such connections prior to sealing the interior cavity closed.

After all necessary connections are made and/or testing is performed, channel cover 114 is assembled in place over channel 160, e.g. against underlapping edge 164. Channel cover 114 has a peripheral edge 116 matching the geometry of channel 160 and a bottom edge 118, which may be an underlapping, overlapping, ramped or sloped edge for mating with shield member 112 such that the three parts 132, 114 and 112 can be sealed together to define interior cavity portions 124a and 124b, which may be a hermetically sealed interior cavity. In this three-part assembly, shield cover 114 and shield member 112 are relatively simple to manufacture, for example using stamping or cutting methods. The shield extender 132 may be a single machined or metal injection molded part that includes the contoured sidewall 140 that may be more difficult to manufacture using other methods and can be configured to include features such as the interior coupling member 168 during the machining process.

Figure 5:
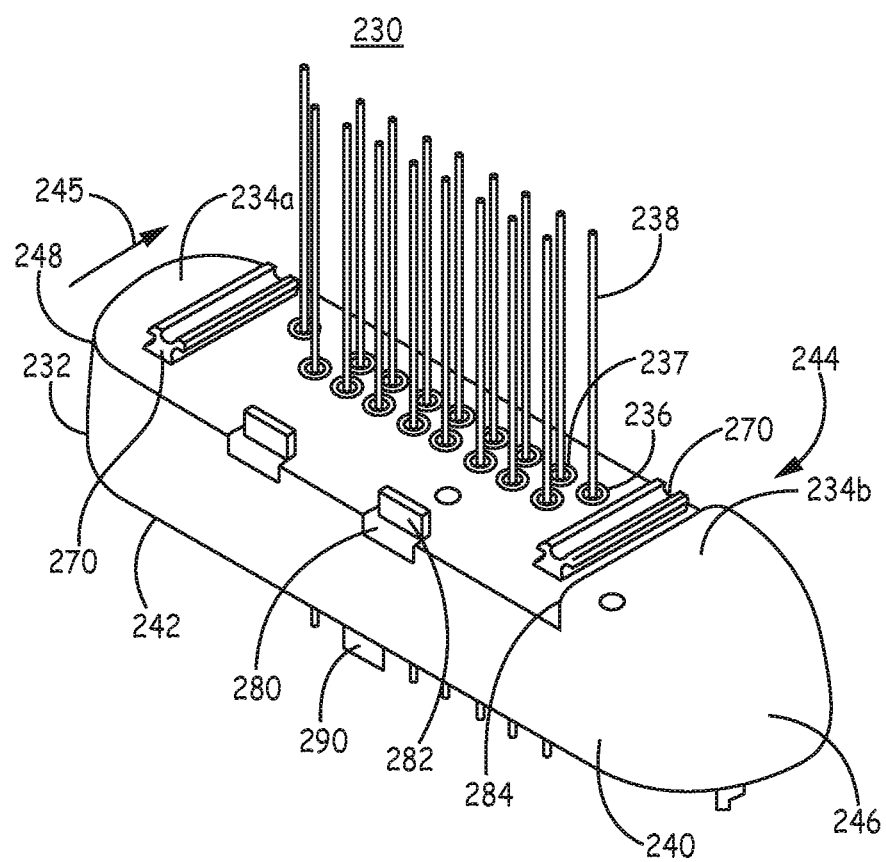
FIG. 5 is a perspective view of a feedthrough assembly according to another exemplary embodiment.
Figure 6A:
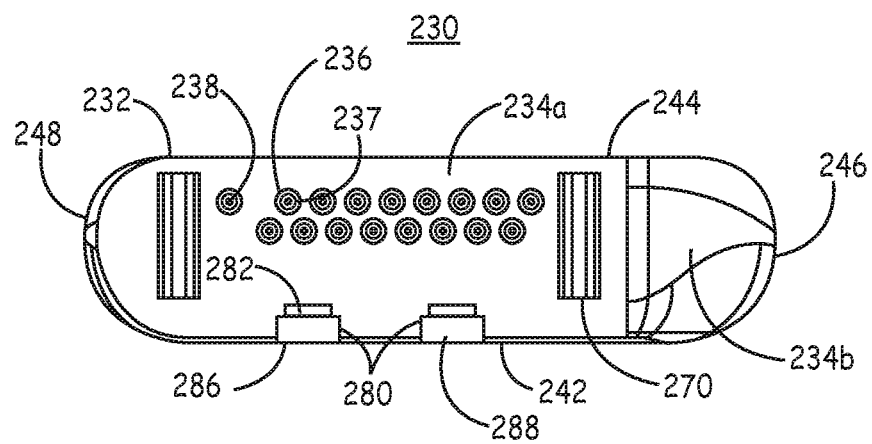
FIGS. 6A through 6C are top, side, and bottom views of the feedthrough assembly shown in FIG. 5.
Figure 6B:
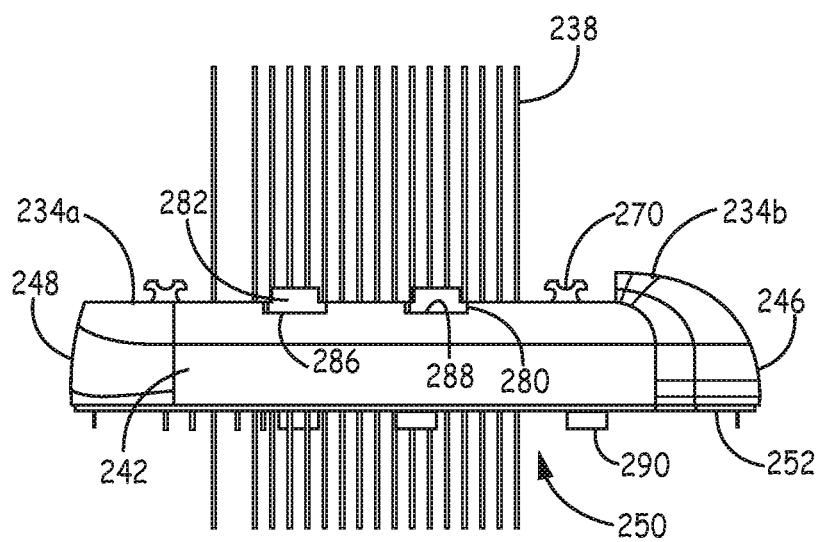
Figure 6C:
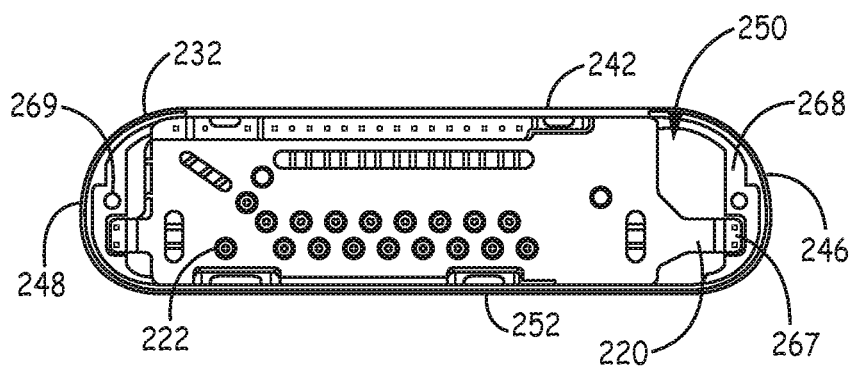

FIG. 5 is a perspective view of a feedthrough assembly 230 according to another example. FIGS. 6A through 6C are top, side and bottom views of the feedthrough assembly 230 shown in FIG. 5. Assembly 230 includes a shield extender 232 having a top face 234a and 234b, collectively 234, and sidewall 240. Sidewall 240 includes opposing major sides 242, 244 and contoured minor sides 246, 248. Sidewall 240 and top face 234 define a portion of the interior cavity of an IMD when assembly 230 is sealed to a shield member as described above.

Top face 234 includes the top face portion 234b which is also referred to herein as a contoured portion 234b that smoothly transitions into minor side 246 and a top surface of an associated connector block that is assembled on top of the substantially flat portion 234a of top face 234. The rounded contoured portion 234b, along with a top side of the associated connector block, forms the top surface of the IMD. In other words, contoured portion 234b is a portion of the exterior surface of the IMD. In other examples, the entirety of top face 234 may interface with the bottom of an associated connector block such that no portion of top face 234 is exposed as an exterior surface of the IMD. In this case, the connector block defines the entire top, contoured, exterior surface of the IMD.

Multiple feedthrough apertures 236 extend through the flat portion 234a. An insulator 237, which may be a glass or ceramic ring and may include a capacitive filter, is positioned in each aperture 236. A feedthrough pin 238 extends through each insulator 237 for carrying electrical signals to/from contacts in an associated connector block from/to the hybrid circuit enclosed by the shield extender 232 and an associated shield member, e.g. as shown in FIG. 1.

Shield extender 232 is shown to include multiple features along top face 234 to facilitate assembling feedthrough assembly 230 with an associated connector block. In the example shown, guide rails 270 extend perpendicularly to the major sides 242, 244 along the flat portion 234a of top face 234. A lateral wall 284 that separates the contoured top portion 234b from the flat portion 234a of top face 234 further serves as an alignment guide when the connector block is advanced over rails 270.

Figure 7:
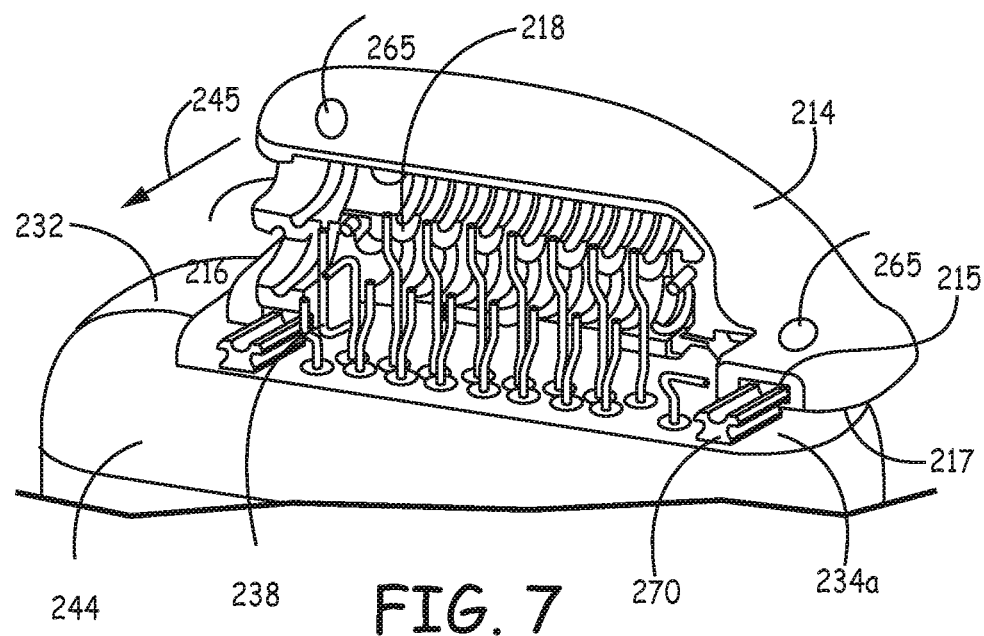
FIG. 7 is a perspective view of a connector block being assembled onto the shield extender of FIGS. 6A-6C.

An associated connector block 214 is shown in FIG. 7 being assembled onto top face 234a of shield extender 232. Connector block 214 includes grooves 215 along a bottom side 217 of the connector block. The grooves 215 have a geometry that mates with rails 270. During an assembly process, the connector block 214 is slid onto the top face flat portion 234a by aligning the connector block grooves 215 with rails 270 and sliding the connector block in the direction from the major side 242 toward major side 244 as shown by arrow 245 (see FIGS. 5 and 7). Each of the guide rails 270 are shown as flared rails having a fluted or grooved top surface in the example shown. The flared rail 270 promotes a snug fit of the connector block 214 against top face flat portion 234a and prevents the connector block 214 from lifting upward off top face flat portion 234a. Rails having other geometries and configurations along top face 234 may be implemented for guiding and retaining a connector block against top face flat portion 234a.

Once assembled on rails 270, the connector block grooves 215 are backfilled with medical adhesive to provide further fixation between shield extender 232 and connector block 214. Alternatively, the connector block 214 and shield extender 232 are overmolded in a multiple shot thermoplastic molding process to hermetically seal connector block 214 and shield extender 232.

During the assembly process, feedthrough pins 238 are electrically coupled to respective contacts 218 of connector block bore(s) 216 and excess length of pins 238 is trimmed. Openings along the connector block 214 that enable electrical connections to be made between pins 238 and connector block contacts 218, e.g. by resistance or laser welding, may be sealed closed using a medical adhesive, such as silicone, or in an overmolding process.

Top face 234 of shield extender 232 may further include mechanical stops, grooves, guides or other fixtures for guiding and retaining an associated connector block. In the illustrative embodiment of FIG. 5 and as shown in FIGS. 6A and 6B, a pair of grooves 280 are provided along the front edge of top face 234 (at the intersection of major side 242 and top face 234) for receiving stopping members of the connector block. Stopping faces 282 of grooves 280 prevent the connector block from being advanced too far in the direction of arrow 245. The stopping faces 282 may additionally be used as welding interfaces for fixation of the connector block to shield extender 232, as described below in conjunction with FIG. 8. As shown in FIG. 5, stopping face 282 may include a tab protruding upward from top face 234 in some embodiments to provide a welding interface.

Shield extender 232 may be a single machined component including various features to guide and retain a connector block along top face 234, such as the flared, grooved rails 270, stopping faces 282, and lateral wall 284 shown in FIGS. 5, 6A and 6B or other rails, ridges, grooves, faces, etc. that may be recessed or protruding features along top face 234 for mating with a corresponding geometry of the associated connector block.

Shield extender 232 may include one or more fixtures or features extending interiorly from the inner surface of top face 234 and/or the inner surface of sidewall 240 and/or from bottom edge 252 defining open bottom side 250. As seen best in the perspective and side views of FIGS. 5 and 6B, respectively, one or more interconnect and fixation tabs 290 may extend downward from bottom edge 252 to provide mechanical fixation to internal components of an associated shield member and may provide an interference fit with the shield member (e.g. shield member 12 of FIG. 1).

As best seen in the bottom view of FIG. 6C, a coupling member or mounting fixture 268 may extend interiorly from sidewall 240 for securing internal IMD circuit boards or other components to shield extender 232. Coupling member 268 includes a fastener receptacle 269, e.g. a screw hole, for receiving a fastener to secure a hybrid circuit board to shield extender 232. Coupling member 268 may include an attachment point 267 for welding or securing a circuit board 220 that includes a contact pad 222 corresponding to each feedthrough pin 238. Electrical connections are made between contact pads 222 and a hybrid circuit board, including control circuitry and other electronics, which is enclosed within shield extender 232 and the associated shield member of the IMD.

As described previously, shield extender 232 may be a single machined or molded component including the various features described above for attaching, coupling, aligning, guiding, or securing other IMD components.

Figure 8:
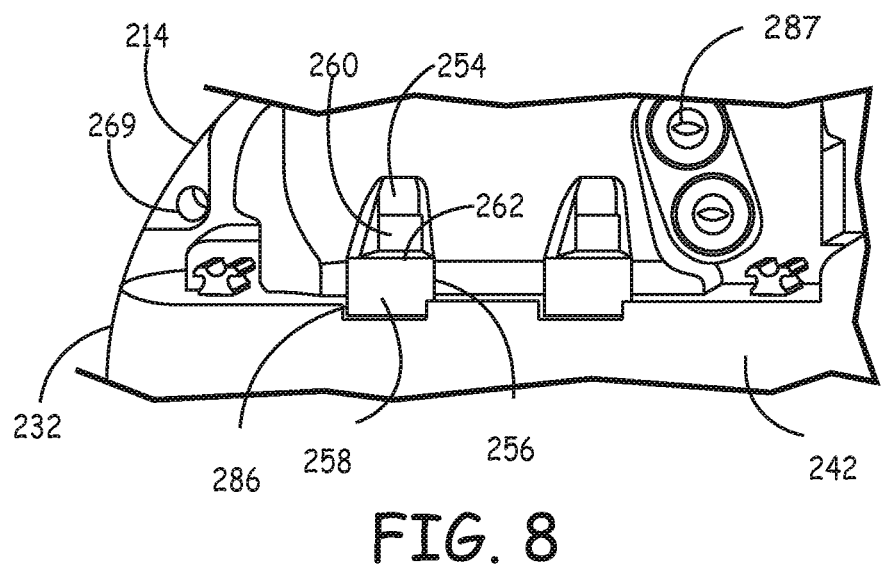
FIG. 8 is an enlarged view of the connector block of FIG. 7 assembled onto the shield extender of FIGS. 6A-6C.

FIG. 8 is an enlarged view of connector block 214 assembled onto shield extender 232. Connector block 214 includes inset grooves 254 that mate with shield extender grooves 280 (seen best in FIGS. 5, 6A and 6B). A weld plate 256 is positioned within each inset groove 254. Weld plates 256 are shown generally "Z" shaped having a first vertical portion 258 to interface with a front face 286 of shield member groove 280, a second vertical portion 260 for interfacing with stopping face 282 of shield member groove 280, and a generally horizontal portion 262 extending from the first vertical portion 258 to the second vertical portion 260.

In one example, first and second vertical portions 258 and 260 of weld plate 256 are welded to shield extender 232 along the front face 286 and the stopping face 282, respectively, of shield extender groove 280. For example, electrodes may be placed against weld plate 256 to resistance weld plate 256 to shield extender 232 through properly positioned openings in connector block inset groove 254. After welding, connector block 214 is held securely against shield extender 232, between weld plate horizontal face 262 and top face 288 of groove 280 (see FIGS. 6A and 6B).

Connector block inset grooves 254 may be filled with medical adhesive or overmolded to seal and embed weld plates 256 within inset grooves 254 to protect the weld joints and provide a smooth exterior surface of connector block 214. Connector block 214 may include exterior features such as a suture through-hole 265 for anchoring the IMD at a desired implant site and set screws 287 for securing a lead connector pin within a connector bore 216 (FIG. 7).

Figure 9:
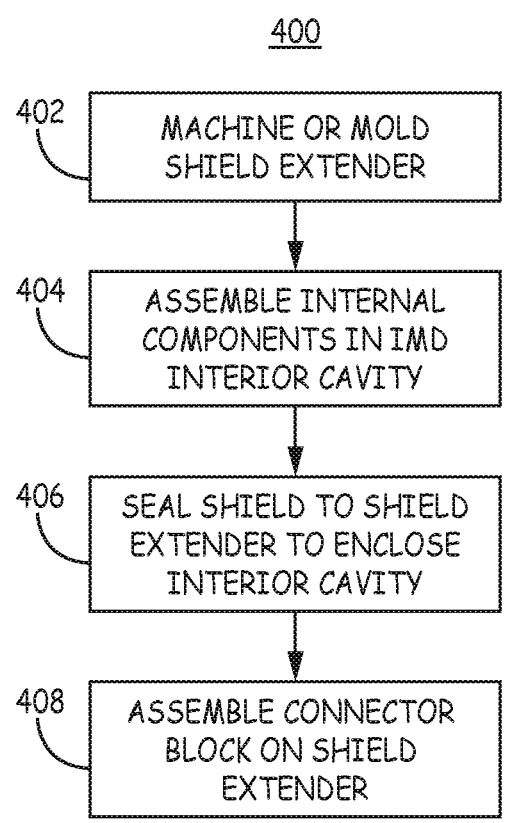
FIG. 9 is a flow chart of a method for manufacturing an IMD.

FIG. 9 is a flow chart of a method 400 for manufacturing an IMD. At block 402, a shield extender is machined or molded having a top face circumscribed by a sidewall as a single continuous piece. The sidewall extends down from the top face and has a bottom edge that defines an open side of the shield extender, opposing the top face as shown and described above, e.g., in FIG. 2. During the machining or molding process, feedthrough apertures are formed through the top face. One or more interior coupling features are formed along an inner surface of the sidewall to facilitate electrical and/or mechanical coupling with interior components. One or more fixtures are formed along the top face for mating with a connector block.

At block 404, internal components, such as a hybrid circuit and battery, are assembled within an interior cavity defined by a housing shield member and the shield extender. For example, a hybrid circuit board is coupled to an interior coupling feature of the shield extender. Electrical connections are made between feedthrough pins passed through the top face of the shield extender and the hybrid circuit.

At block 406, the shield member is sealed to the shield extender, e.g. by laser or resistance welding to enclose the IMD interior cavity, thereby enclosing the internal IMD components. The shield member defines a first portion of the interior cavity and the shield extender defines a second portion of the interior cavity.

In examples that enable a medical electrical lead to be coupled to the IMD, a connector block is assembled onto the top face of the shield extender at block 408. Methods and features used to assemble the connector block onto the shield extender have been described above in conjunction with FIGS. 7 and 8.

Thus, various embodiments of an IMD housing that includes a skirted feedthrough assembly have been presented in the foregoing description with reference to specific embodiments. The various embodiments of the feedthrough assembly described herein are associated with manufacturing methods that can result in a device of reduced overall size and/or cost. It is appreciated that various modifications to the referenced embodiments may be made without departing from the scope of the disclosure as set forth in the following claims.

What is claimed is:

1. An implantable medical device, comprising:
an electronic circuit;
a shield member defining a first portion of an interior cavity of the implantable medical device;
a feedthrough assembly comprising:
a shield extender having a top face and a sidewall that extends from the top face so that the top face and the sidewall are a single continuous component, wherein the shield extender defines a channel in the sidewall,
at least one feedthrough aperture within the shield extender,
an insulated feedthrough pin extending through the feedthrough aperture,
the sidewall having a bottom edge that defines an open side of the shield extender, the bottom edge coupled to the shield member,
the sidewall defining a second portion of the interior cavity, the second portion in communication with the first portion, the electronic circuit residing in the interior cavity, the second portion of the interior cavity being accessible through the channel,
the feedthrough pin being electrically coupled to the electronic circuit, the electronic circuit enclosed in the interior cavity; and
a connector block for receiving a medical lead coupled to the top face of the shield extender.

2. The implantable medical device of claim 1, wherein the top face provides a top surface of the shield extender and wherein the at least one feedthrough aperture extending through the top surface.

3. The implantable medical device of claim 1, at least a portion of the electronic circuit resides in the second portion of the interior cavity.

4. The implantable medical device of claim 1, wherein the shield extender sidewall has an outer surface defining an exterior surface of the implantable medical device.

5. The implantable medical device of claim 1, wherein the shield extender further comprises a coupling member extending interiorly from the sidewall and accessible through the channel.

6. The implantable medical device of claim 5, wherein the coupling member defines an opening for receiving a fastener.

7. The implantable medical device of claim 6, wherein the electronic circuit is coupled to the coupling member.

8. The implantable medical device of claim 6, wherein the shield member comprises a sidewall having a longitudinal extension configured to mate with shield extender channel to enclose the second portion of the interior cavity.

9. The implantable medical device of claim 1, wherein the top face comprises a contoured portion defining an outer surface of the implantable medical device.

10. The implantable medical device of claim 1, further comprising:
a connector block for receiving a medical lead coupled to the top face of the shield extender; and
a fixture along the top face of the shield extender for interfacing with the connector block.

11. The implantable medical device of claim 10, wherein the fixture comprises at least one of a rail, a stopping interface, and a groove.

12. An implantable medical device, comprising:
an electronic circuit;
a shield member defining a first portion of an interior cavity of the implantable medical device; and
a feedthrough assembly comprising:
a shield extender having a top face providing a top surface of the shield extender and a sidewall that extends from the top face so that the top face and the sidewall are a single continuous component, wherein the shield extender defines a channel in the sidewall,
at least one feedthrough aperture extending through the top surface provided by the top face,
an insulated feedthrough pin extending through the feedthrough aperture,
the sidewall having a bottom edge that defines an open side of the shield extender, the bottom edge coupled to the shield member,
the sidewall defining a second portion of the interior cavity, the second portion in communication with the first portion, the electronic circuit residing in the interior cavity,
the feedthrough pin being electrically coupled to the electronic circuit, the electronic circuit enclosed in the interior cavity.

13. The implantable medical device of claim 12, wherein the second portion of the interior cavity is accessible through the channel.

14. The implantable medical device of claim 13, at least a portion of the electronic circuit resides in the second portion of the interior cavity.

15. The implantable medical device of claim 14, wherein the electronic circuit is coupled to the coupling member.

16. The implantable medical device of claim 12, wherein the shield extender sidewall has an outer surface defining an exterior surface of the implantable medical device.

17. The implantable medical device of claim 12, wherein the shield extender further comprises a coupling member extending interiorly from the sidewall and accessible through the channel.

18. The implantable medical device of claim 17, wherein the coupling member defines an opening for receiving a fastener.

19. The implantable medical device of claim 12, wherein the shield member comprises a sidewall having a longitudinal extension configured to mate with the shield extender channel to enclose the second portion of the interior cavity.

20. An implantable medical device, comprising:
an electronic circuit;
a shield member defining a first portion of an interior cavity of the implantable medical device;
a feedthrough assembly comprising:
a shield extender having a top face and a sidewall that extends from the top face so that the top face and the sidewall are a single continuous component, wherein the shield extender defines a channel in the sidewall,
at least one feedthrough aperture within the shield extender,
an insulated feedthrough pin extending through the feedthrough aperture,
the sidewall having a bottom edge that defines an open side of the shield extender, the bottom edge coupled to the shield member,
the sidewall defining a second portion of the interior cavity, the second portion in communication with the first portion, at least a portion of the electronic circuit residing in the second portion of the interior cavity, the second portion of the interior cavity being accessible through the channel,
the feedthrough pin being electrically coupled to the electronic circuit, the electronic circuit enclosed in the interior cavity.

* * * * *